(12) United States Patent
Easley et al.

(10) Patent No.: US 10,874,554 B2
(45) Date of Patent: Dec. 29, 2020

(54) OPHTHALMIC SURGICAL INSTRUMENT

(71) Applicant: XRV-IP, LLC, Chesterfield, MO (US)

(72) Inventors: James C. Easley, Cottleville, MO (US); Matt LaConte, Chesterfield, MO (US)

(73) Assignee: XRV-IP, LLC, Chesterfield, MO (US)

( * ) Notice: Subject to any disclaimer, the term of this patent is extended or adjusted under 35 U.S.C. 154(b) by 198 days.

(21) Appl. No.: 16/008,644

(22) Filed: Jun. 14, 2018

(65) Prior Publication Data
US 2019/0380869 A1 Dec. 19, 2019

(51) Int. Cl.
*A61F 9/008* (2006.01)

(52) U.S. Cl.
CPC .................... *A61F 9/008* (2013.01)

(58) Field of Classification Search
CPC ........................................ A61F 9/008
USPC ............................................. 606/4
See application file for complete search history.

(56) References Cited

U.S. PATENT DOCUMENTS

| 5,409,453 A * | 4/1995 | Lundquist ......... A61M 25/0138 604/22 |
| 6,450,948 B1 * | 9/2002 | Matsuura ............. A61B 1/0055 600/139 |
| 6,984,230 B2 | 1/2006 | Scheller et al. |
| 9,370,447 B2 | 6/2016 | Mansour |

* cited by examiner

*Primary Examiner* — Aaron F Roane
(74) *Attorney, Agent, or Firm* — Armstrong Teasdale LLP

(57) ABSTRACT

A probe tip assembly includes an optical fiber for channeling light energy and a straightening tube circumscribing at least a portion of the optical fiber. The straightening tube includes a first metallic material and is moveable between a first position and a second position. The tip assembly also includes a guiding member circumscribing the optical fiber and the straightening tube. The guiding member includes a second metallic material and a curvable portion configurable between a pre-formed curved state defining a radius of curvature and a straightened state. The guiding member also includes a plurality of notches, wherein, as the straightening tube is retracted from the first position to the second position, the guiding member transitions from its straightened state to its pre-formed curved state.

36 Claims, 9 Drawing Sheets

OPHTHALMIC SURGICAL INSTRUMENT

BACKGROUND

The field of the disclosure relates generally to medical devices, and more specifically, to medical devices used in ophthalmology.

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

During such laser photocoagulation procedures, a surgeon aims the laser (via an optical fiber) at a plurality of targets within the eye, e.g., by guiding or moving the laser from a first target to a second target within the eye. As such, control of movement of the laser by the surgeon is significant to a successful procedure. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF DESCRIPTION

In one aspect of the present disclosure, a probe tip assembly includes an optical fiber for channeling light energy and a straightening tube circumscribing at least a portion of the optical fiber. The straightening tube includes a first metallic material and is moveable between a first position and a second position. The tip assembly also includes a guiding member circumscribing the optical fiber and the straightening tube. The guiding member includes a second metallic material and a curvable portion configurable between a pre-formed curved state defining a radius of curvature and a straightened state. The guiding member also includes a plurality of notches, wherein, as the straightening tube is retracted from the first position to the second position, the guiding member transitions from its straightened state to its pre-formed curved state.

In another aspect of the present disclosure, a surgical instrument is provided. The surgical instrument includes a handle assembly having an actuation member. The surgical instrument also includes a tip assembly including an optical fiber for channeling light energy and a straightening tube coupled to the actuation member and circumscribing at least a portion of the optical fiber. The straightening tube includes a first metallic material and is moveable between a first position and a second position. The tip assembly also includes a guiding member circumscribing the optical fiber and the straightening tube. The guiding member includes a second metallic material and a curvable portion configurable between a pre-formed curved state defining a radius of curvature and a straightened state. The guiding member includes a plurality of notches, wherein, as the straightening tube is retracted from the first position to the second position, the guiding member transitions from its straightened state to its pre-formed curved state.

Figure 1:
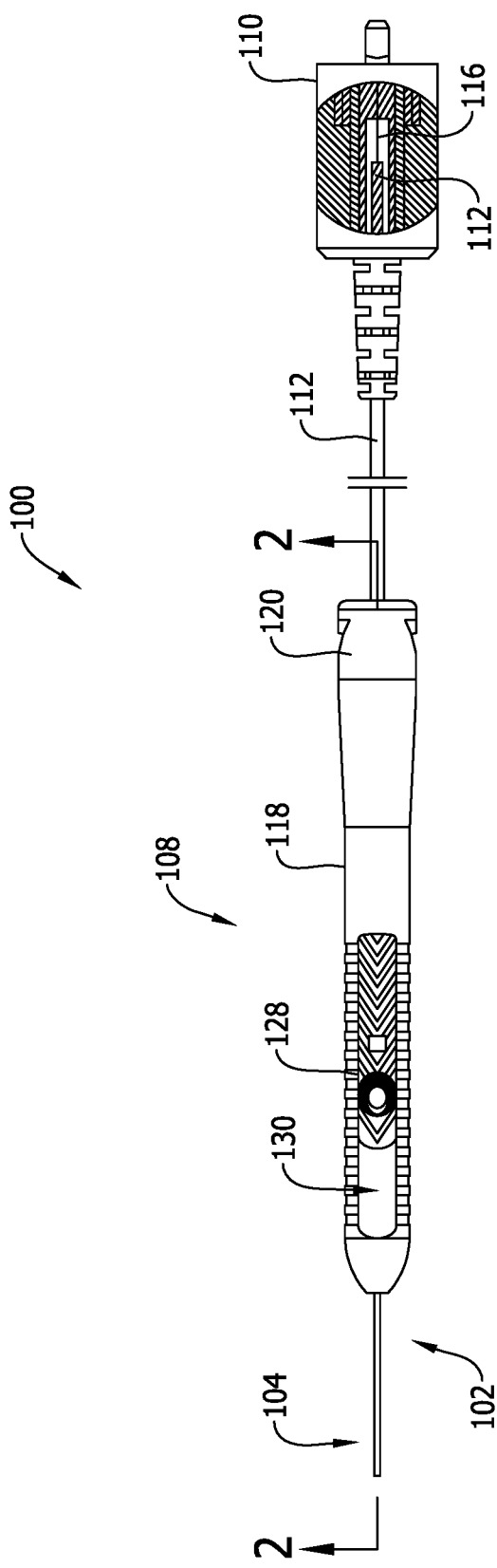
FIG. 1 is an exemplary embodiment of a top view of an exemplary ophthalmic surgical instrument having an exemplary probe tip assembly in a straightened position in accordance with the present disclosure.

Although specific features of various embodiments may be shown in some drawings and not in others, this is for convenience only. Any feature of any drawing may be referenced and/or claimed in combination with any feature of any other drawing.

DETAILED DESCRIPTION

The present disclosure is directed to ophthalmologic surgical instruments, and more specifically, to ophthalmologic laser probes. The examples described herein include an ophthalmologic surgical instrument including a probe tip assembly having an optical fiber for channeling light energy and a straightening tube circumscribing at least a portion of the optical fiber. The straightening tube includes a first metallic material and is moveable between a first position and a second position. The tip assembly also includes a guiding member circumscribing the optical fiber and the straightening tube. The guiding member includes a second metallic material and a curvable portion configurable between a pre-formed curved state defining a radius of curvature and a straightened state. The guiding member also includes a plurality of notches, wherein, as the straightening tube is retracted from the first position to the second position, the guiding member transitions from its straightened state to its pre-formed curved state.

The ophthalmologic surgical instrument described herein includes a nitinol guiding member having a pre-formed curvable portion that is straightened with an inner rigid straightening tube that also contains the optical fiber within the straightening tube. Retraction of the inner rigid tube allows the nitinol material of the guiding member to return to its relaxed, curved state. The nitinol material stiffness is reduced within the curvable portion of the guiding member by cutting a series of closely spaces slots or notches along the inner curvature surface perpendicular to a centerline axis of the guiding member. The reduction in stiffness enables the smaller diameter straightening tube to fully straighten the nitinol guiding member as the straightening tube is extended through the guiding member. As such, the notches reduce the stiffness of the guiding member to a level below that of the straightening tube to allow the straightening tube to transition the curved portion of the guiding member from its curved state to its straightened state as the straightening tube is moved from its retracted second position to its extended first position.

In some embodiments of the present disclosure, the medical device includes an ophthalmologic device, an optometric device, a probe, a vitrectomy device, a microsurgical device, an endoscopic surgical device, a neurosurgical device, or a plastic surgical device. In some embodiments, the medical device is used an as instrument, such as a microsurgical instrument, in an operation (e.g., surgery) conducted in or around an eye. The device is used, for example, in surgical treatment of retinal diseases, as for example resulting from hypertonia, or other vascular changes.

Figure 2:
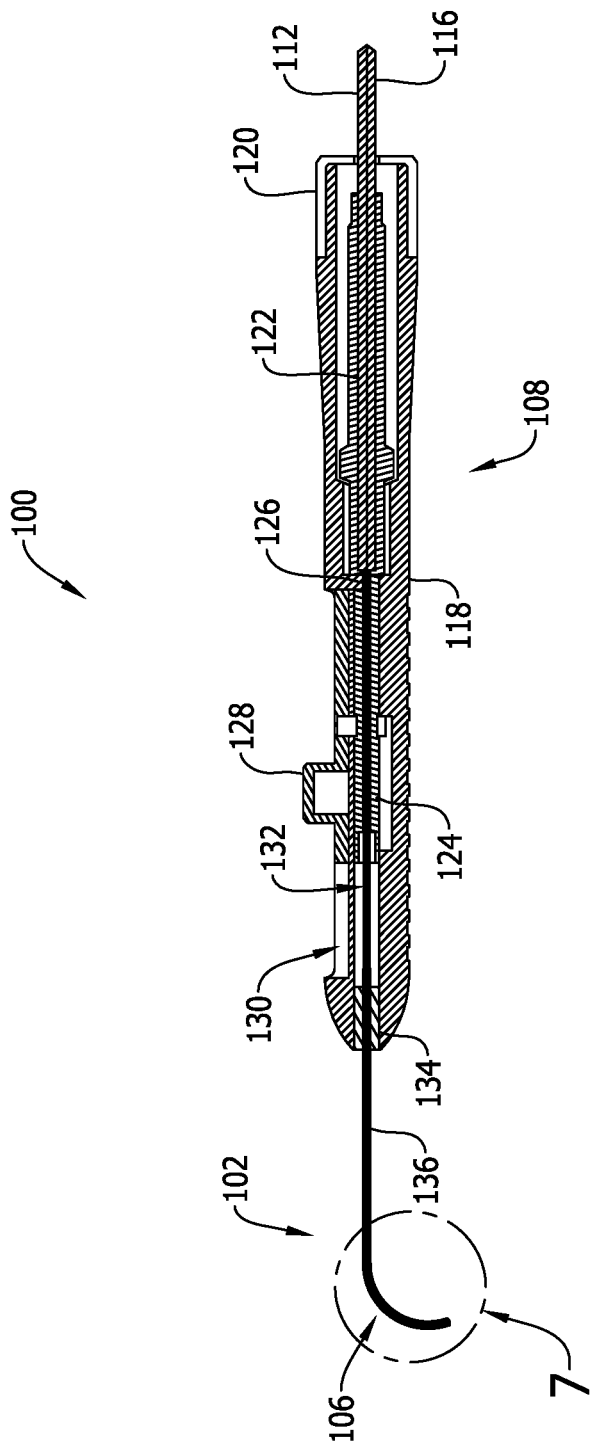
FIG. 2 is an exemplary embodiment of a cross-sectional view of the ophthalmic surgical instrument shown in FIG. 1 with the probe tip assembly in a curved position in accordance with the present disclosure.

FIG. 1 is a top view of an exemplary ophthalmic surgical instrument 100 having an exemplary probe tip assembly 102. FIG. 1 illustrates probe tip assembly 102 in a straightened position 104. FIG. 2 is a cross-sectional view of ophthalmic surgical instrument 100 illustrating probe tip assembly 102 in a curved position 106. In the exemplary embodiment, ophthalmic surgical instrument 100 includes a handle assembly 108 attached to a base portion 110 via a conduit 112. Base portion 110 is also referred to as an optical connector and is removably coupled to a laser source (not shown) and configured to receive a laser beam (not shown) that is applied to an end of an optical fiber 116. Optical fiber 116 extends through base portion 110, conduit 112, handle assembly 108, and into probe tip assembly 102. Conduit 112, also referred to as a buffer or a sheath is a pliable material used to protect optical fiber 16. As shown in FIG. 2, handle assembly 108 includes a handle portion 118 through which optical fiber 116 extends. A collar 120 is coupled to handle portion 118 opposite tip assembly 102. A fiber anchor 122 is positioned within handle portion 118 and anchors optical fiber 116 to handle assembly 108 to prevent movement of optical fiber 116 with respect to handle assembly 108. Handle assembly 108 also includes a stepped tube 124 positioned within handle portion 118 and separated axially along optical fiber 116 from fiber anchor 122 by a bushing 126. An actuation mechanism 128 is coupled to handle portion 118 and slides along a slot 130 defined in handle portion 118 to actuate a straightening tube 132 of probe tip assembly 102. As shown in FIG. 2, handle portion 118 also includes a nose bushing 134 that couples a guiding member 136 of probe tip assembly 102 to handle portion 118 and through which straightening tube 132 is actuated.

Figure 3:
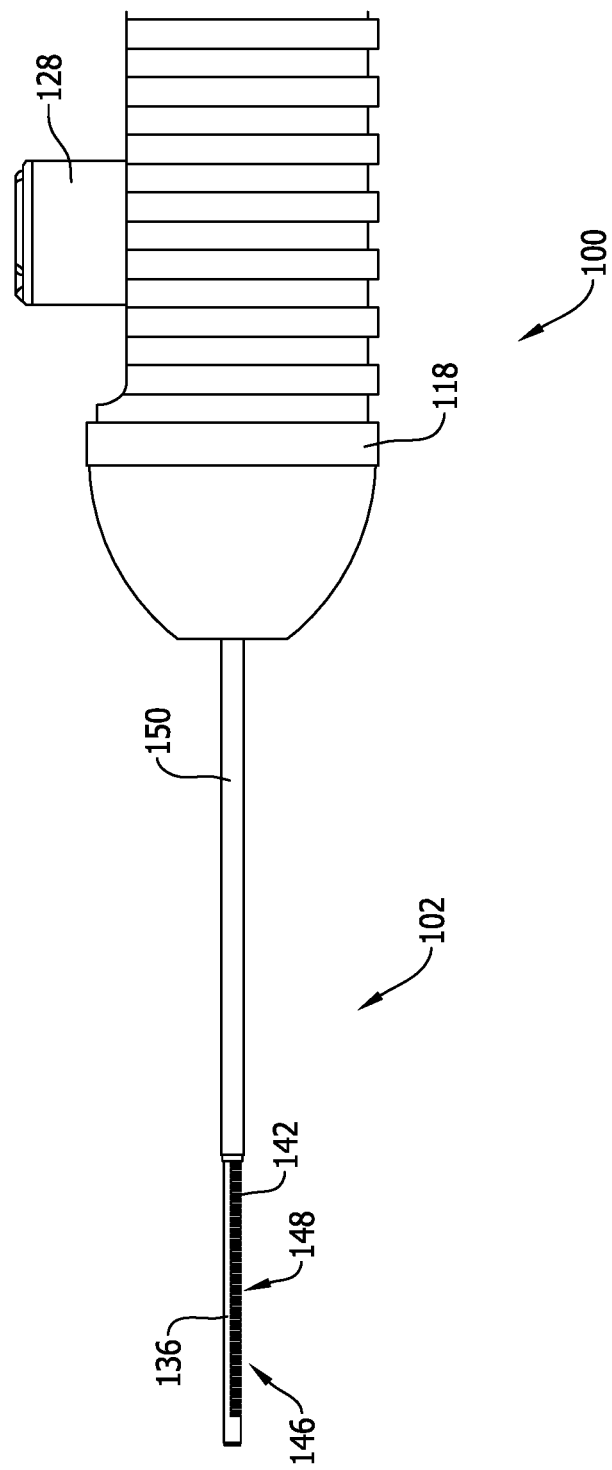
FIG. 3 is an exemplary embodiment of an enlarged view of the ophthalmic surgical instrument shown in FIG. 1 with the probe tip assembly in the straightened position in accordance with the present disclosure.
Figure 4:
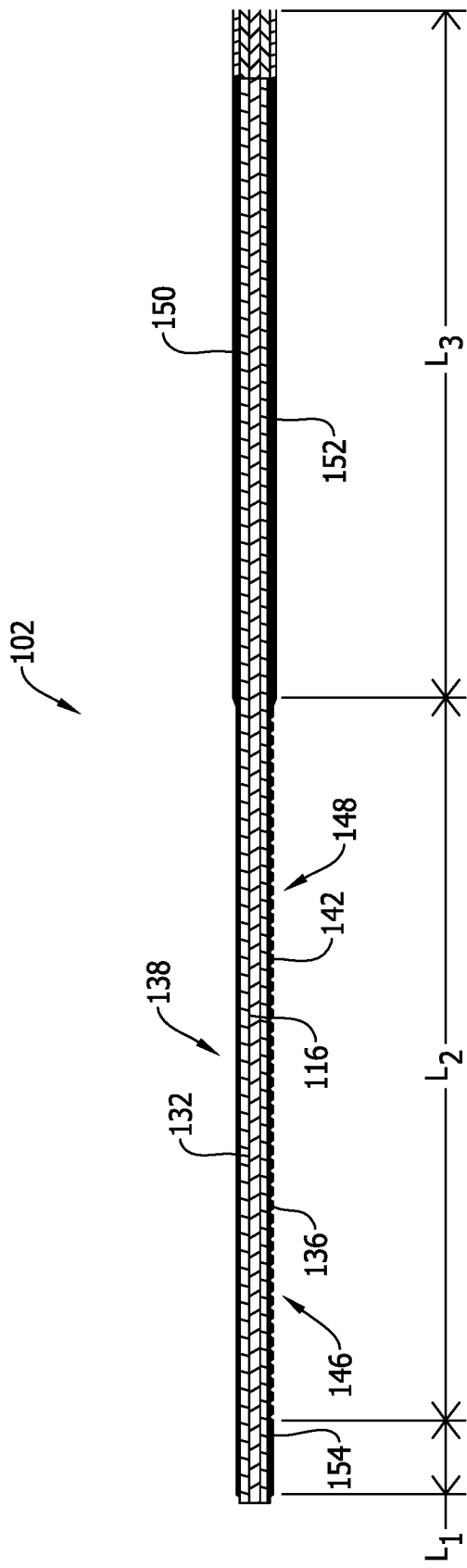
FIG. 4 is an exemplary embodiment of a cross-sectional view of the probe tip assembly shown in FIG. 3 illustrating the probe tip assembly in the straightened position in accordance with the present disclosure.
Figure 5:
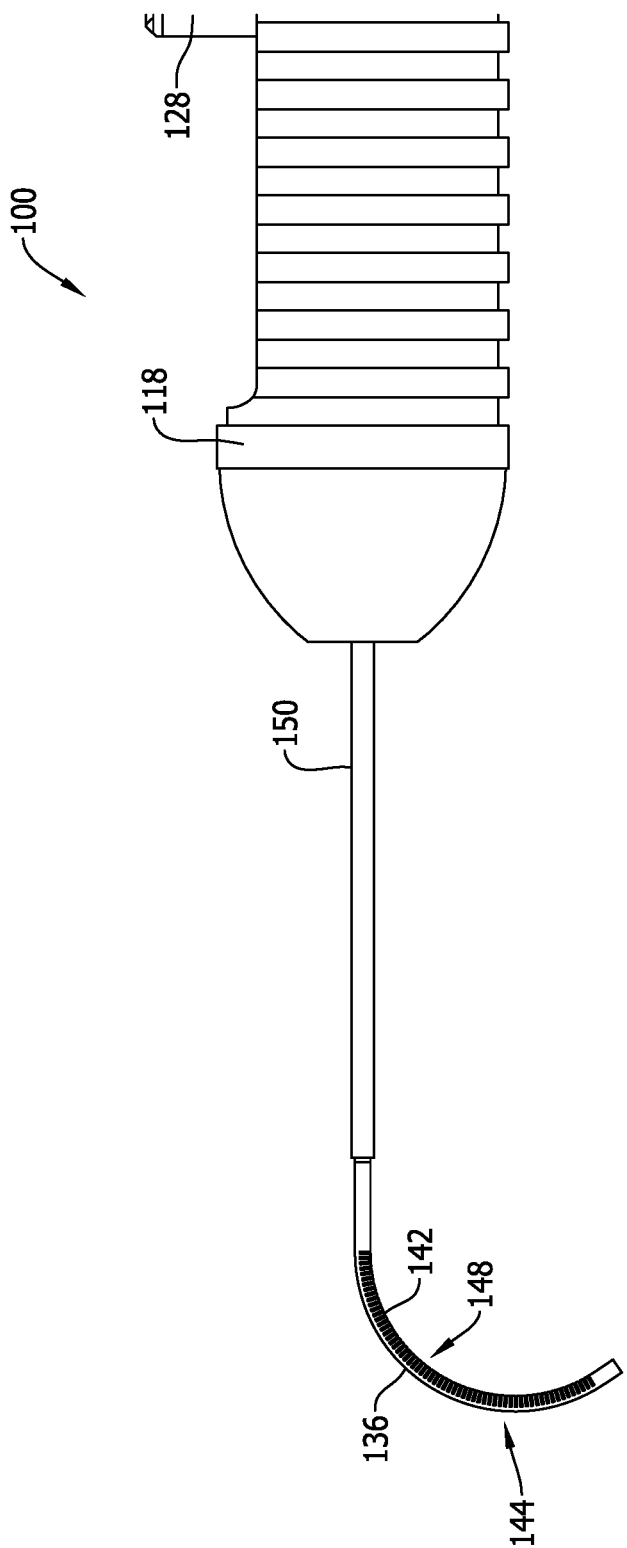
FIG. 5 is an exemplary embodiment of an enlarged view of the ophthalmic surgical instrument shown in FIG. 1 with the probe tip assembly in the curved position in accordance with the present disclosure.
Figure 6:
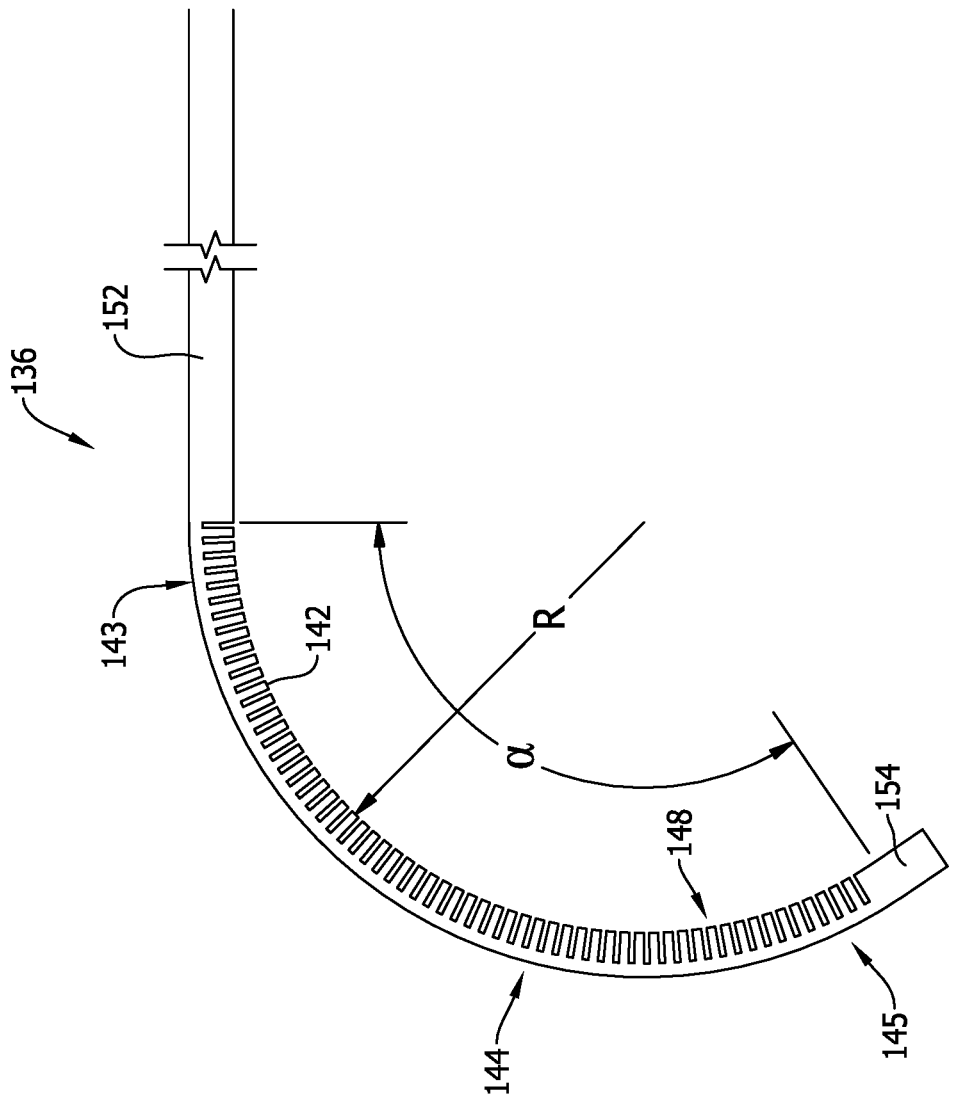
FIG. 6 is an exemplary embodiment of an enlarged view of the probe tip assembly in the curved position in accordance with the present disclosure.
Figure 7:
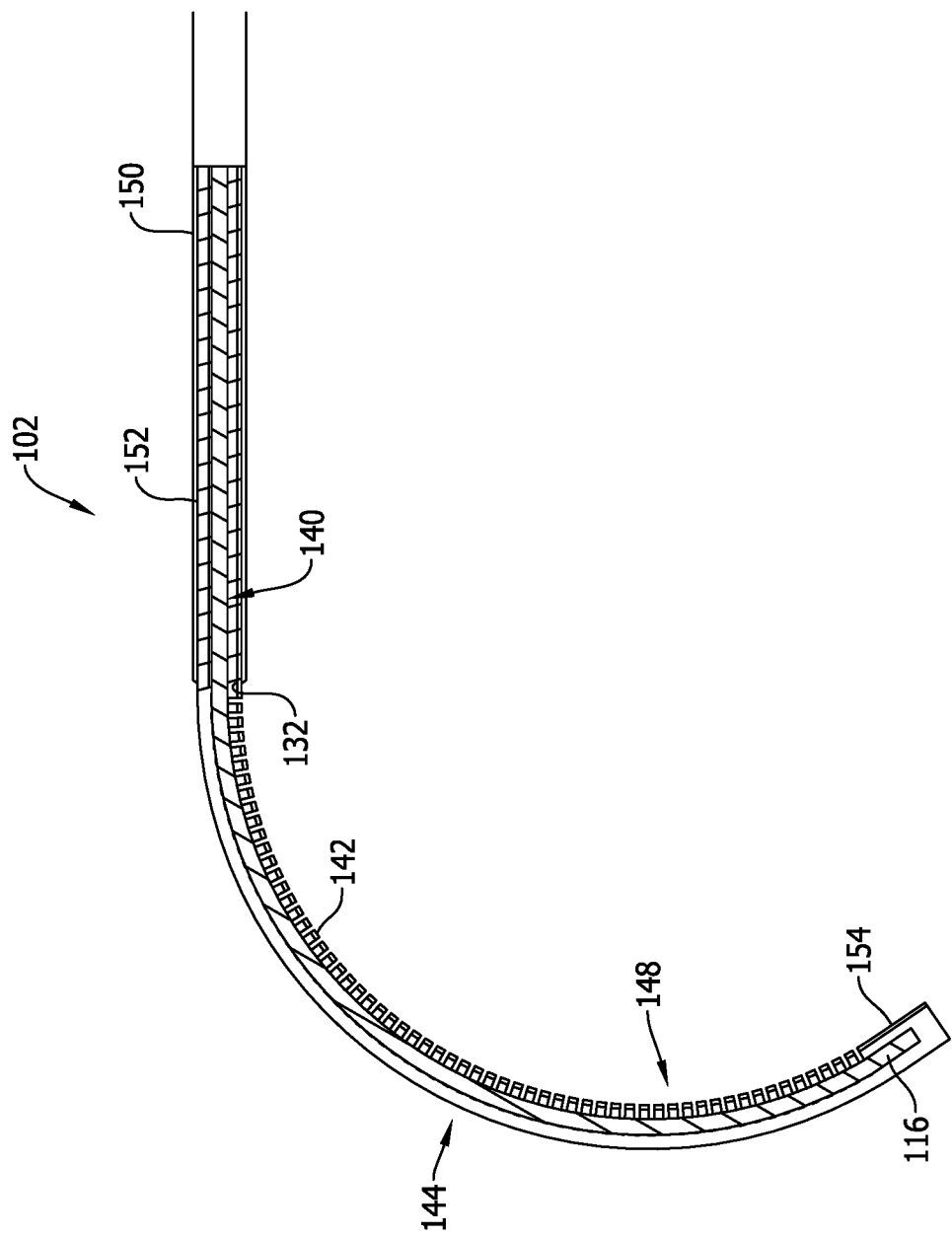
FIG. 7 is an exemplary embodiment of a cross-sectional view of the probe tip assembly shown in FIG. 6 illustrating the probe tip assembly in the curved position in accordance with the present disclosure.

FIG. 3 is an enlarged view of ophthalmic surgical instrument 100 with probe tip assembly 102 in the straightened position 104, and FIG. 4 is a cross-sectional view of probe tip assembly 102 in the straightened position 104. FIG. 5 is an enlarged view of ophthalmic surgical instrument 100 with probe tip assembly 102 in the curved position 106, FIG. 6 is an enlarged view of probe tip assembly 102 in the curved position 106, and FIG. 7 is a cross-sectional view of probe tip assembly 102 in the curved position 106.

In the exemplary embodiment, probe tip assembly 102 includes optical fiber 116 configured to channel light energy from a laser beam to a distal end of optical fiber inside of a patient's eye. Probe tip assembly 102 also includes straightening tube 132 circumscribing at least a portion of optical fiber 116. As described herein, straightening tube 132 is formed from a metallic material and is moveable between a first, extended, position 138 and a second, retracted position 140. Guiding member 136 circumscribes both optical fiber 116 and straightening tube 132 and is also formed from a metallic material. In the exemplary embodiment, guiding member 136 includes a curvable portion 142 that is configurable between a pre-formed curved state 144 defining a radius of curvature R and a straightened state 146. Guiding member 136 includes a plurality of notches 148 that facilitate transitioning between the straightened state 146 and the curved stated 144. In operation, as straightening tube 132 is retracted from its first position 138 to its second position 140, guiding member 136 transitions from its straightened state 146 to its curved stated 144. As such, when straightening tube 132 is in its first position 138, curvable portion 142 is in its straightened state 146, and when straightening tube 132 is in its second position 140, curvable portion 142 is in its curved state 144.

In some embodiments, probe tip assembly 102 also includes an outer support tube 150 circumscribing guiding member 136. In other embodiments, probe tip assembly 102 does not include outer support tube 150 and guiding member 136 is directly coupled to handle portion 108 via bushing 134.

As best shown in FIG. 4, guiding member 136 also includes a rigid portion 152 positioned proximal to curvable portion 142 and a tip portion 154 positioned distal to curvable portion 142. Rigid portion 152 and tip portion are free of notches 148 such that radius of curvature R (shown in FIGS. 6 and 7) is defined by curvable portion 142 having notches 148. Furthermore, tip portion 154 defines a first length L1 along guiding member 136 while curvable portion 142 defines a second length L2 longer than first length L1, and rigid portion 152 defines a third length L3 longer than second length L2.

In the exemplary embodiment, straightening tube 132 is formed from a rigid metallic material, such as stainless steel, and guiding member 136 is formed from a flexible metallic material. More specifically, guiding member 136 is formed from nitinol and is pre-formed to include curvable portion 142 in its natural, relaxed state. As described herein nitinol is used to form guiding member 136 because nitinol is able to hold a more aggressive curve (smaller radius) than other known materials, such as plastic. As such, the use of nitinol makes for a more useful device because less material is required bend optical fiber 116 to its desired angle.

As shown in FIGS. 6 and 7, curvable portion 142 defines a radius of curvature R within a range of from about 0.10 inches to about 0.40 inches, from about 0.15 inches to about 0.35 inches, from about 0.20 inches to about 0.30 inches, or about 0.25 inches. Furthermore, curvable portion 142 includes a first end 143 proximate rigid portion 152 and a second end 145 proximate tip portion 154. In the exemplary embodiment, curvable portion 142 defines an angle α between first end 143 and second end 145 when curvable portion 142 is in its pre-formed curved state 144. More specifically, angle α is within a range of from about 110 degrees to about 200 degrees, from about 130 degrees to about 170 degrees, from about 140 degrees to about 160 degrees, or about 150 degrees in curved state 144. That is, when straightening tube 132 is in its fully extended first position 138, angle α is zero degrees because all of straightening tube 132, guiding member 136 and optical fiber 116 are concentric. As straightening tube 132 is retracted towards its second position 140, curvable portion 132 begins to revert to its curved stated 144 and angle α increases to its maximum value when straightening tube 132 is in its fully retracted second position.

Figure 8:
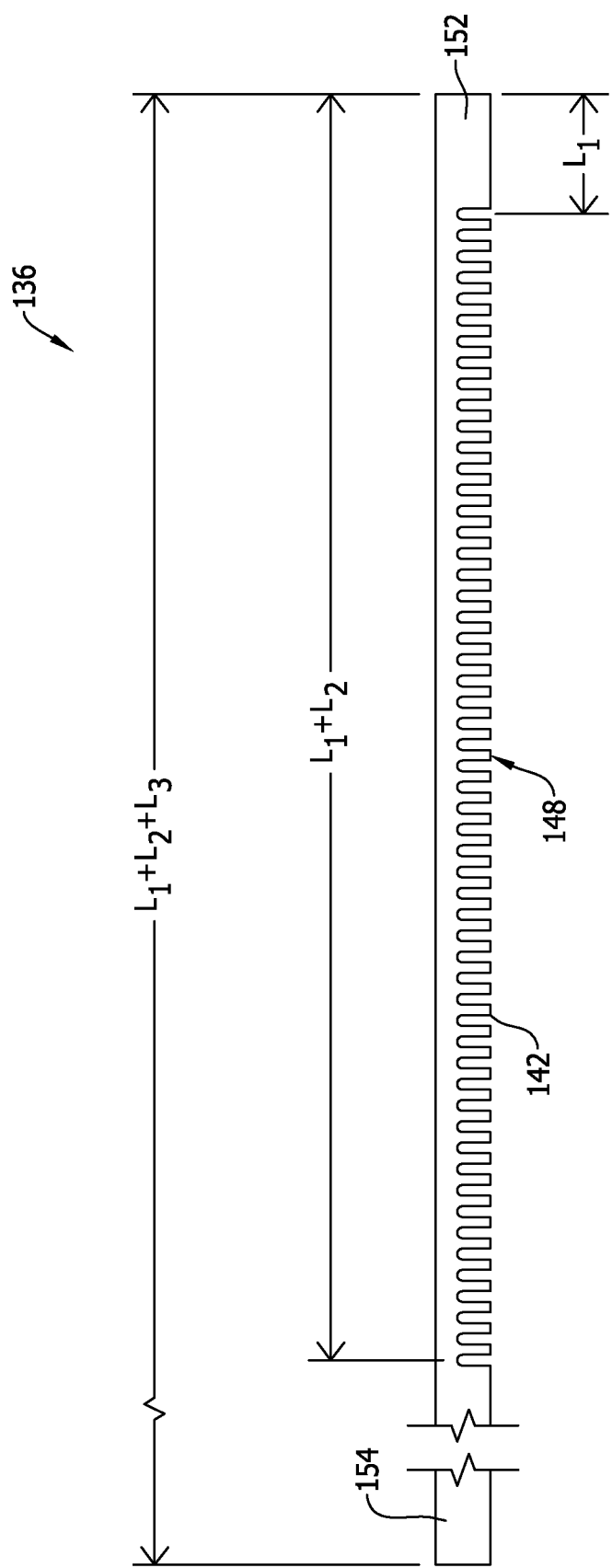
FIG. 8 is an exemplary embodiment of a side view of an exemplary guiding member of the probe tip assembly shown in FIG. 4 in accordance with the present disclosure.
Figure 9:
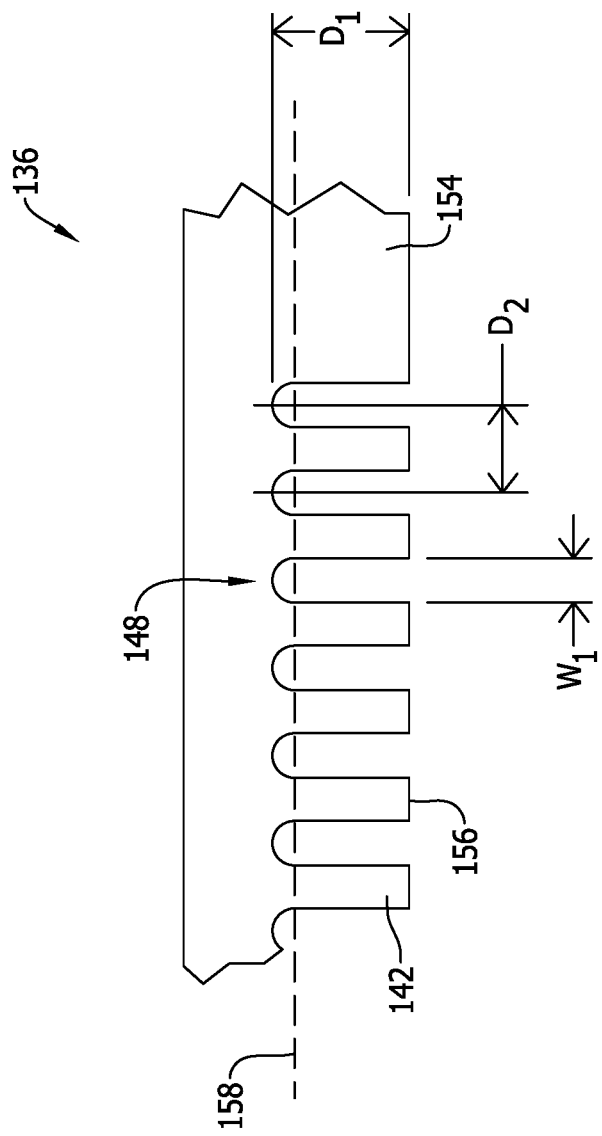
FIG. 9 is an exemplary embodiment of an enlarged view of the guiding member shown in FIG. 9 illustrating a plurality of notches in accordance with the present disclosure.

FIG. 8 is a side view of guiding member 136 of probe tip assembly 102, and FIG. 9 is an enlarged view of guiding member 136 illustrating plurality of notches 148 in in curvable portion 142. Notches 148 are formed in guiding member 136 in order to reduce the stiffness of the nitinol guiding member 136. The reduction in stiffness enables the smaller diameter straightening tube 132 to fully straighten the nitinol guiding member 136 as straightening tube 132 is extended through guiding member 136. As such, notches 148 reduce the stiffness of guiding member 136 to a level below straightening tube 132 to allow straightening tube 132 to transition curved portion 142 of guiding member 136 from its curved state 144 to its straightened state 146 as straightening tube 132 is moved from its second position 140 to its first position 138.

As shown in FIG. 9, each notch 148 defines a width W1 of from about 0.0005 inches to about 0.0050 inches, from about 0.0010 inches to about 0.0040 inches, from about 0.0020 inches to about 0.0030 inches, or about 0.0025 inches. The wider the width of each notch 148, the greater the reduction in stiffness of curvable portion 142 and the smaller the potential radius of curvature R. However, width W1 of each notch 148 is less than a diameter of optical fiber 116 to prevent optical fiber 116 from exiting guiding member 136 through a notch 148. Furthermore, each notch defines a notch depth D1 of from about 0.010 inches to about 0.015 inches as measured from an outer surface 156 of guiding member 136 towards a centerline 158 of guiding member 136. More specifically, notches 148 are formed in an inner diameter of the radius of curvature R of curvable portion 142. Similarly, the deeper the depth of each notch 148, the greater the reduction in stiffness of curvable portion 142 and the smaller the potential radius of curvature R. Additionally, notches 148 defined a distance D2 within a range of from about 0.0060 inches to about 0.010 inches, from about 0.0070 inches to about 0.0090 inches, or about 0.0080 inches from a center of one notch 148 to a center of an immediately adjacent notch 148. Moreover, each notch 148 includes a pair of semicircular ends 160 that define a full radius. More specifically, ends 160 are defined by a radius taken along centerline 158 such that each notch 148 extends approximately half a circumference of guiding member 136. Generally, notches 148 include any desired depth, width, and spacing to prove curvable portion 142 of guiding member 136 with a predetermined desired radius of curvature R and stiffness.

Exemplary embodiments of the ophthalmic surgical instrument are described above in detail. The ophthalmic surgical instrument and its components are not limited to the specific embodiments described herein, but rather, components of the instrument may be utilized independently and separately from other components described herein. For example, the components may also be used in combination with other medical devices and systems, methods, and apparatuses, and are not limited to practice with only the systems and methods as described herein. Rather, the exemplary embodiments can be implemented and utilized in connection with many other applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the disclosure, including the best mode, and to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A probe tip assembly comprising:
   an optical fiber for channeling light energy;
   a straightening tube circumscribing at least a portion of the optical fiber, wherein the straightening tube comprises a first metallic material and is moveable between a first position and a second position;
   a guiding member circumscribing the optical fiber and the straightening tube, wherein the guiding member comprises a second metallic material and comprises a curvable portion configurable between a pre-formed curved state defining a radius of curvature and a straightened state, wherein the guiding member comprises a plurality of notches, wherein, as the straightening tube is retracted from the first position to the second position, the guiding member transitions from its straightened state to its pre-formed curved state, wherein when a distal end of the straightening tube is retracted to a proximal end of the curvable portion, the straightening tube allows the curvable portion of the guiding member to assume the pre-formed curved state by not providing a force on the curvable portion of guiding member.

2. The assembly of claim 1, wherein when the straightening tube is in the first position, the curvable portion is straight, and when the straightening tube is retracted to the second position, the curvable portion is curved.

3. The assembly of claim 1, wherein the guiding member comprises a rigid portion positioned proximal to the curvable portion, and a tip portion positioned distal to the curvable portion.

4. The assembly of claim 3, wherein the tip portion and the rigid portion are free of notches.

5. The assembly of claim 3, wherein the tip portion has a first length, the curved portion has a second length greater than the first length, and the rigid portion has a third length longer than the second length.

6. The assembly of claim 1, wherein the first metallic material comprises stainless steel.

7. The assembly of claim 1, wherein the second metallic material comprises nitinol.

8. The assembly of claim 1, wherein each notch of the plurality of notches defines a notch width and the optical fiber defines a diameter greater than the notch width.

9. The assembly of claim 1, wherein the notch width is between 0.0005 inches and 0.0050 inches.

10. The assembly of claim 1, wherein each notch of the plurality of notches defines a notch depth between 0.010 inches and 0.015 inches measured from an outer surface of the guiding member towards a centerpoint of the guiding member.

11. The assembly of claim 1, wherein the plurality of notches define a distance of between 0.006 inches and 0.010 inches from a center of a first notch to a center of an adjacent notch.

12. The assembly of claim 1, wherein each notch of the plurality of notches extends half a circumference of the guiding member.

13. The assembly of claim 1, wherein the plurality of notches are formed in an inner diameter of the radius of curvature of the curvable portion.

14. The assembly of claim 1, wherein each notch of the plurality of notches includes a pair of semicircular ends.

15. The assembly of claim 1, wherein the radius of curvature of the curvable portion is between 0.10 inches and 0.40 inches.

16. The assembly of claim 1, wherein the curvable portion comprises a first end and a second end, and wherein an angle defined between the first end and the second in the curved state is between 110 degrees and 200 degrees.

17. The assembly of claim 1, wherein the straightening tube and the guiding member are immediately radially adjacent each other.

18. The assembly of claim 1, wherein an external surface of the straightening tube contacts an internal surface of the guiding member when the straightening tube is in the first position and the guiding member is in the straightened state.

19. The assembly of claim 1, wherein the optical fiber and the guiding member are in a face-to-face relationship when the straightening tube is in the second position.

20. The assembly of claim 1, wherein when the distal end of the straightening tube is retracted proximal to a most proximal notch, the straightening tube allows the guiding member to assume the pre-formed curved state by not providing a force on the guiding member.

21. A surgical instrument comprising:
a handle assembly comprising an actuation member; and
a tip assembly comprising:
an optical fiber for channeling light energy;
a straightening tube coupled to the actuation member and circumscribing at least a portion of the optical fiber, wherein the straightening tube comprises a first metallic material and is moveable between a first position and a second position; and
a guiding member circumscribing the optical fiber and the straightening tube, wherein the guiding member comprises a second metallic material and a curvable portion configurable between a pre-formed curved state defining a radius of curvature and a straightened state, wherein the guiding member comprises a plurality of notches, wherein, as the straightening tube is retracted from the first position to the second position, the guiding member transitions from its straightened state to its pre-formed curved state, wherein when a distal end of the straightening tube is retracted proximal of a distal end of the curvable portion, the straightening tube allows the curvable portion of the guiding member to assume the pre-formed curved state by not providing a force on the guiding member distal of the distal end of the straightening tube.

22. The instrument of claim 21, wherein the first metallic material comprises stainless steel.

23. The instrument of claim 21, wherein the second metallic material comprises nitinol.

24. The instrument of claim 21, wherein each notch of the plurality of notches defines a notch width and the optical fiber defines a diameter greater than the notch width.

25. The instrument of claim 21, wherein the notch width is between 0.0005 inches and 0.0050 inches.

26. The instrument of claim 21, wherein each notch of the plurality of notches defines a notch depth between 0.010 inches and 0.015 inches measured from an outer surface of the guiding member towards a centerpoint of the guiding member.

27. The instrument of claim 21, wherein the plurality of notches define a distance of between 0.006 inches and 0.010 inches from a center of a first notch to a center of an adjacent notch.

28. The instrument of claim 21, wherein each notch of the plurality of notches extends half a circumference of the guiding member.

29. The instrument of claim 21, wherein the plurality of notches are formed in an inner diameter of the radius of curvature of the curvable portion.

30. The instrument of claim 21, wherein each notch of the plurality of notches includes a pair of semicircular ends.

31. The instrument of claim 21, wherein the radius of curvature of the curvable portion is between 0.10 inches and 0.40 inches.

32. The instrument of claim 21, wherein the curvable portion comprises a first end and a second end, and wherein an angle defined between the first end and the second in the curved state is between 110 degrees and 200 degrees.

33. The instrument of claim 21, wherein when the straightening tube is in the first position, the curvable portion is straight, and when the straightening tube is retracted to the second position, the curvable portion is curved.

34. The instrument of claim 21, wherein the guiding member comprises a rigid portion positioned proximal to the curvable portion, and a tip portion positioned distal to the curvable portion.

35. The instrument of claim 34, wherein the tip portion and the rigid portion are free of notches.

36. The instrument of claim 34, wherein the tip portion has a first length, the curved portion has a second length greater than the first length, and the rigid portion has a third length longer than the second length.

* * * * *